United States Patent [19]

Cliffe et al.

[11] Patent Number: 4,760,158
[45] Date of Patent: Jul. 26, 1988

[54] NITRILES

[75] Inventors: Ian A. Cliffe, Cippenham; Richard S. Todd, Burnham, Nr. Slough, both of England

[73] Assignee: John Wyeth & Brother Limited, Maidenhead, England

[21] Appl. No.: 23,329

[22] Filed: Mar. 9, 1987

[30] Foreign Application Priority Data

Mar. 13, 1986 [GB] United Kingdom ............ 8606255

[51] Int. Cl.[4] ........................... C07C 121/46
[52] U.S. Cl. .................... 558/303; 546/245; 558/369; 558/431; 558/432
[58] Field of Search ............ 558/432, 431, 303

[56] References Cited

U.S. PATENT DOCUMENTS

| | | | |
|---|---|---|---|
| 2,425,029 | 8/1947 | Cass | 558/460 |
| 2,993,068 | 7/1961 | Schipper | 558/431 X |
| 4,442,122 | 4/1984 | Engelhart et al. | 558/303 X |

OTHER PUBLICATIONS

C. A., 102: 95510c, Overman et al., (1985).
C. A., 83: 42876j; Larcheveque, et al., (1975).
C. A., 81: 120399f, Larcheveque, et al., (1974).
Makosza and Serafin, Chem. Abstracts, vol. 66, 94792x, (1967).
Steiner et al., Chem. Abstracts, vol. 77, 57976s, (1972).

*Primary Examiner*—Joseph Paul Brust
*Attorney, Agent, or Firm*—Richard K. Jackson

[57] ABSTRACT

Novel 3-halo-2,2-disubstituted propanenitriles of formula

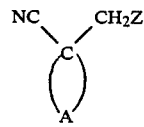

wherein Z represents bromo or chloro and A, together with the carbon atom to which it is attached, represents a 5,6 or 7 membered saturated carbocyclic or heterocyclic ring, are useful as intermediates for preparing substituted pyrimido[1,2-a]indoles. The intermediates can be prepared by a novel process which comprises condensing a 2,2-disubstituted ethanenitrile with a dihalomethane in the presence of a non-nucleophilic strong base.

6 Claims, No Drawings

NITRILES

This invention relates to 3-halo-2,2-disubstituted-propanenitriles and a process for their preparation.

The present invention provides novel 3-halo-2,2-disubstituted-propanenitriles of the general formula (I)

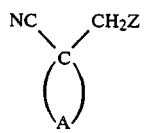

(wherein Z represents bromo or chloro and A together with the carbon atom to which it is attached represents a 5, 6 or 7 membered saturated carbocyclic or heterocyclic ring). These novel compounds are valuable intermediates, for example, in the synthesis of substituted pyrimido[1,2-a]indoles (as described in the specification of our copending application Ser. No. 23,333 entitled "Substituted Pyrimidoindoles" filed concurrently with this application, under applicants' reference H-372 and claiming priority from U.K. Patent Application No. 8606254).

According to this copending application the substituted pyrimidoindole products can be prepared by the following reaction scheme

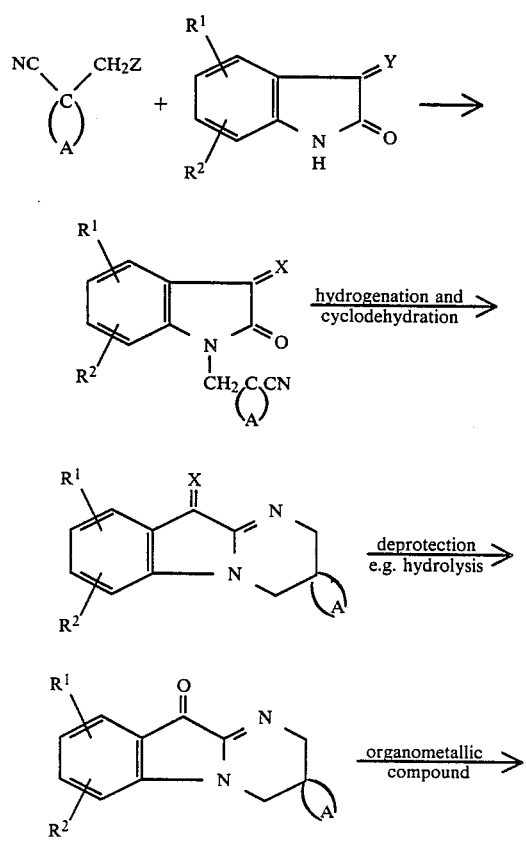

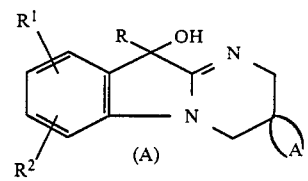

In this reaction scheme Z and A have the meanings given above, $R^1$ and $R^2$ each represent hydrogen, hydroxyl, lower alkyl, lower alkoxy, halo(halower)alkyl, halogen amino or mono or di(lower)alkylamino, Y is oxo or protected oxo, X is protected oxo and R is lower alkyl or a mono- or bi-cyclic aryl radical. As disclosed in the copending application the pyrimidoindole products of formula A are useful as hypoglycaemic agents. The various processes in the reaction scheme may be carried out as disclosed in the copending application; the processes are analogous to those disclosed in our U.S. Pat. No. 1,366,133.

The term "lower" as used herein means that the radical referred to contains 1 to 6 carbon atoms. For example, a lower alkyl group may be methyl, ethyl, propyl or butyl. Preferably A together with the carbon atom to which it is attached represents a cycloalkyl radical such as cyclohexyl (which may be substituted by one or more alkyl substituents). When A together with the carbon atom to which it is attached represents a saturated heterocyclic ring the hetero atom may be, for example, an oxygen or nitrogen atom and in the latter instance the nitrogen atom should be substituted during the process of the invention by, for example, alkyl or by a protecting group (such as 1,1-dimethylethoxycarbonyl, benzyl or trimethylsilyl) which may subsequently be removed to give a product in which the nitrogen atom is unsubstituted.

We have found that the compounds of the present invention may be prepared by a novel process which comprises condensing a 2,2-disubstituted ethanenitrile of general formula (II)

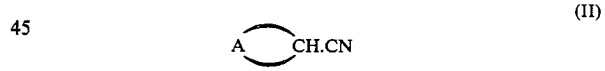

where A had the meaning given above with bromochloromethane, dibromomethane or dichloromethane in the presence of a non-nucleophilic strong base. Preferably the ethanenitrile is reacted with bromochloromethane. We have found that bromochloromethane gives substantially higher yields than either dichloromethane or dibromomethane.

The literature method for preparing 3-chloro-2,2-dialkylpropanenitriles, which are related to the compounds of formula I, is a photochemical chlorination of, for example, 2,2-dimethylpropanenitrile followed by a fractional distillation to separate the mixture containing the starting material, the desired product and the isomers of di- and trichloro-2,2-dimethylpropanenitrile (U.S. Pat. No. 2,425,029). This reaction is very slow and gives a mixture of products, the yields of the desired product being low. We have found that the process of the present invention enables the compounds of formula (I) to be prepared in high yields and in short reaction time.

It is known that dibromo- or dichloromethanes (but not bromochloromethanes) react with 2-arylethanenitriles using bases such as sodium hydroxide or sodium amide [Makosza et al Acta Pol. Pharm., 1972, 29, 235 (Chem. Abs., 78, 57976) and Roczniki Chem., 1966, 40, 1647 (Chem. Abs., 66, 94792)]. Under these conditions the products obtained from the aryl substituted nitriles depended upon the starting materials. In some instances the product was the monohalide whilst in other instances the product was the dinitrile. We have found that use of a non-nucleophilic strong base with the nitrile of formula (II) gives high yields of the desired product.

The non-nucleophilic base is chosen so as to form the carbanion of the nitrile of formula

(where A is as defined above). Suitable bases include alkali metal amides of formula MW wherein M is sodium, potassium or lithium (preferably lithium) and W is a secondary amine such as a dialkylamine [e.g. diethylamine, diisopropylamine, ditertiarybutylamine, di-n-decylamine, dicyclohexylamine, N-t-amyl-N-t-butylamine, N-isopropyl-N-cyclohexylamine or N-(1'-ethylcyclohexyl)-1,1,3,3-tetramethylbutylamine] or a cyclic compound, e.g. piperidine or 2,2,6,6-tetramethylpiperidine. A preferred metal amide is lithium diisopropylamide.

The process of the invention may be carried out in an inert solvent such as tetrahydrofuran, toluene, hexane, ether or hydrocarbon mixtures at reaction temperatures of, for example, $-80°$ C. to $25°$ C., preferably $-65°$ to $15°$ C.

The following Examples illustrate the invention:

EXAMPLE 1

1-Chloromethylcyclopentanecarbonitrile

A solution of cyclopentanecarbonitrile (14.3 g, 150 mmol) in THF (25 ml) was added dropwise to a stirred solution of lithium diisopropylamide (158 mmol) in THF (150 ml) and hexane (100 ml), under dry nitrogen, keeping the temperature below $-65°$. After 0.5 h, the solution was warmed to ambient temperature and added to a stirred solution of bromochloromethane (49.4 ml, 750 mmol) in THF (50 ml) keeping the temperature below $-65°$. The solution was allowed to warm to ambient temperature and, after 18 h, poured into water (500 ml). The aqueous mixture was extracted with $CHCl_3$ (3×250 ml). The extracts were washed with 2N HCl (100 ml) and $H_2O$ (100 ml), dried ($MgSO_4$), and evaporated under reduced pressure to give an oil which was distilled to give a pale yellow oil (8.9 g) b.p. $96°$ at 10 mmHg.

Found: C, 59.0; H, 7.3; N, 9.5%.

$C_7H_{10}ClN$ requires: C, 58.6; H, 7.0; N, 9.75%.

EXAMPLE 2

1-Chloromethylcycloheptanecarbonitrile

A solution of cycloheptanecarbonitrile (12.3 g, 100 mmol) in THF (50 ml) was added dropwise to a well stirred solution of lithium diisopropylamide (105 mmol) in THF/hexane (75 ml/60 ml) under nitrogen, keeping the temperature at $-65°$. After 1 h, the solution was allowed to warm to ambient temperature and added dropwise to a well stirred solution of bromochloromethane (32.5 ml; 500 mmol) in THF (50 ml) under nitrogen keeping the temperature between $-50°$ and $-60°$. After 10 min, the solution was allowed to warm to ambient temperature, poured into water (250 ml) and the aqueous mixture extracted with chloroform (3×150 ml). The extracts were washed with 2N-HCl (2×50 ml), saturated aq. $NaHCO_3$ (100 ml), and water (100 ml), then dried ($MgSO_4$) and evaporated under reduced pressure to give a brown oil (18.0 g). Distillation gave the title compound (12.65 g), b.p. $78°-80°$ at 0.25 mmHg.

Found: C, 63.3; H, 8.45; N, 8.4%.

$C_9H_{14}ClN$ requires: C, 63.0; H, 8.2; N, 8.2%.

EXAMPLE 3

1-Chloromethylcyclohexanecarbonitrile

METHOD A 1.5M-BuLi in hexane (13 ml) was added dropwise to a stirred solution of diisopropylamine (2.8 ml) in dry THF (20 ml) at $-78°$ under nitrogen. After 10 min at $-78°$, the solution was warmed to $0°$, then cooled to $-65°$ and a solution of cyclohexane carbonitrile (2.18 g) in dry THF (5 ml) was added dropwise, and the solution stirred for 20 min at $-70°$. The solution was transferred into a solution of bromochloromethane (26 g) in dry THF (10 ml) at $-70°$ under nitrogen. Once the addition was complete, the solution was warmed to room temperature, poured into $H_2O$ (100 ml) and extracted with $CH_2Cl_2$ (3×100 ml). The organic layer was separated, washed with 2N-HCl (20 ml) and $H_2O$ (2×50 ml), and dried ($MgSO_4$). Evaporation of the solvent under reduced pressure gave a yellow oil (2.5 g), which was distilled under reduced pressure to give the pure title compound, (0.79 g), b.p. $66°$ at 0.3 mmHg.

Found: C, 61.4; H, 7.71; N, 8.98%.

$C_8H_{12}ClN$ requires: C, 61.0; H, 7.67; N, 8.89%.

METHOD B

A solution of cyclohexanecarbonitrile (2.73 g, 25 mmol) in toluene (20 ml) was added dropwise to a solution of lithium diisopropylamide (25 mmol) in toluene/hexanes (isomeric mixture) (20 ml/17 ml) at $0°$ under nitrogen. The stirred mixture was warmed at room temperature, after 30 min cooled to $0°$, treated dropwise with a solution of bromochloromethane (3.24 g, 25 mmol) in toluene (5 ml), after 5 min warmed to room temperature, and, after 18 h, treated with water (50 ml) with vigorous stirring. The aqueous phase was separated, extracted with toluene (50 ml), and the toluene solution dried ($MgSO_4$) and evaporated in vacuo to leave a brown oil (3.75 g). Short-path distillation gave the title compound (2.86 g, 72.5%) as a colourless oil, b.p. $83°-86°/0.23$ mmHg.

EXAMPLE 4 tert-Butyl-4-chloromethyl-4-cyanopiperidine-1-carboxylate

1. A solution of di-tert-butyldicarbonate (4.36 g) in $CH_2Cl_2$ (10 ml) was added dropwise to a stirred solution of 4-cyanopiperidine (2.42 g) in $CH_2Cl_2$ (50 ml). After 2 hours the solvent was evaporated under reduced pressure and the residual oil dissolved in ethyl acetate (50 ml). The solution was cooled to $0°$, washed rapidly with an ice-cold solution of $KHSO_4$ (0.136 g) in water (100 ml), washed with saturated aq. $NaHSO_4$ (50 ml), dried (MgSO4), and evaporated under reduced pressure to give 1-tert-butyloxycarbonyl-4-cyanopiperidine (4.02 g), m.p. 48°–50°.

Found: C, 63.0; H, 8.8; N, 13.2%.

$C_{11}H_{18}N_2O_2$ requires: C, 62.8; H, 8.6; N, 13.3%.

2. A solution of 1.42M-BuLi in hexane (7.75 ml) was added dropwise to a stirred solution of diisopropylamine (1.1 g) in tetrahydrofuran (30 ml) at −50° under nitrogen. The solution was warmed to 0°, cooled to −65°, and a solution of 1-tert-butyloxycarbonyl-4-cyanopiperidine (2.1 g) in tetrahydrofuran (20 ml) added dropwise, such that the temperature remained below −65°. The mixture was warmed to ambient temperature, cooled to −65°, and added dropwise to a stirred solution of bromochloromethane (6.47 g), in tetrahydrofuran (10 ml) under nitrogen such that the temperature remained below −65°. The mixture was warmed to ambient temperature, poured into water (20 ml), and extracted with chloroform (3×100 ml). The chloroform extracts were washed with ice-cold 0.011M-potassium hydrogen sulphate solution (1000 ml) and saturated aqueous sodium hydrogen carbonate (100 ml), dried (MgSO4), and evaporated under reduced pressure to give an oil (2.8 g) which slowly crystallised. The solid was purified by trituration with hexane, chromatography (SiO2; Et2O) and recrystallisation from diethyl ether-hexane to give the title compound (1.02 g), m.p. 114.5°–115.5°.

Found: C, 56.1; H, 7.55; N, 10.6%.

$C_{12}H_{19}ClN_2O_2$ requires: C, 55.7; H, 7.4; N, 10.8%.

EXAMPLE 5

Reaction of cyclohexanecarbonitrile with bromochloromethane, dibromomethane and dichloromethane A solution of cyclohexanecarbonitrile (5.45 g, 50 mmol) in toluene (25 ml) was added dropwise to a solution of lithium diisopropylamide (52.5 mmol) in toluene/hexanes (isomeric mixture) (40 ml/36 ml) at −65° under nitrogen. After 1 h, the solution was warmed to room temperature, cooled to −65°, and added dropwise to a stirred solution of dihalomethane (250 mmol) in toluene (20 ml) under nitrogen, maintaining the temperature at ca −65°. After 1 h, the mixture was allowed to warm to ambient temperature, treated with water (120 ml), and the layers separated. The aqueous phase was extracted with toluene (100 ml) and the toluene layer and extract dried (MgSO4) and evaporated in vacuo to leave an oil. Distillation gave the required products as indicated below:

| Reactant | | Product | | |
|---|---|---|---|---|
| Dihalo-methane | Quantity Used | Yield (as indicated by GLC) | Yield (isolated) | Bp (°C./mmHg) |
| CH2Br2 | 43.5 g | A 61% | 3.61 g, 36% | 70–77°/0.019[a] |
| CH2BrCl | 32.4 g | B 80% | 4.91 g, 62% | 118–120°/13 |
| CH2Cl2 | 21.3 g | B 50% | 2.46 g, 31% | 95–103°/0.5[a] |

([a]Bath temp.)
A = 1-bromomethylcyclohexanecarbonitrile
B = 1-chloromethylcyclohexanecarbonitrile A similar process carried out in tetrahydrofuran as solvent, instead of toluene/hexanes, under standard conditions (using lithium diisopropylamide as base and a reaction temperature of −65° C.) gave a GLC yield of 10% when dibromomethane was the reactant and a GLC yield of 80% when bromochloromethane was the reactant.

We claim:

1. A compound of formula (I)

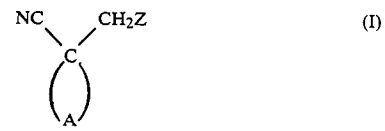

wherein

Z represents bromo or chloro; and

A, together with the carbon atom to which it is attached, represents cyclopentane, cyclohexane or cycloheptane, or the corresponding carbocyclic rings substituted by one or two alkyl groups, independently, containing from 1 to 6 carbon atoms.

2. A compound as claimed in claim 1 wherein A represents —(CH2)5—.

3. A compound according to claim 1 which is 1-chloromethylcyclopentanecarbonitrile.

4. A compound according to claim 1 which is 1-chloromethylcycloheptanecarbonitrile.

5. A compound according to claim 1 which is 1-chloromethylcyclohexanecarbonitrile.

6. A compound according to claim 1 which is 1-bromomethylcyclohexanecarbonitrile.

* * * * *